March 2, 1971 C. R. MAXAM Plant Pat. 3,035
APPLE TREE
Filed March 29, 1968
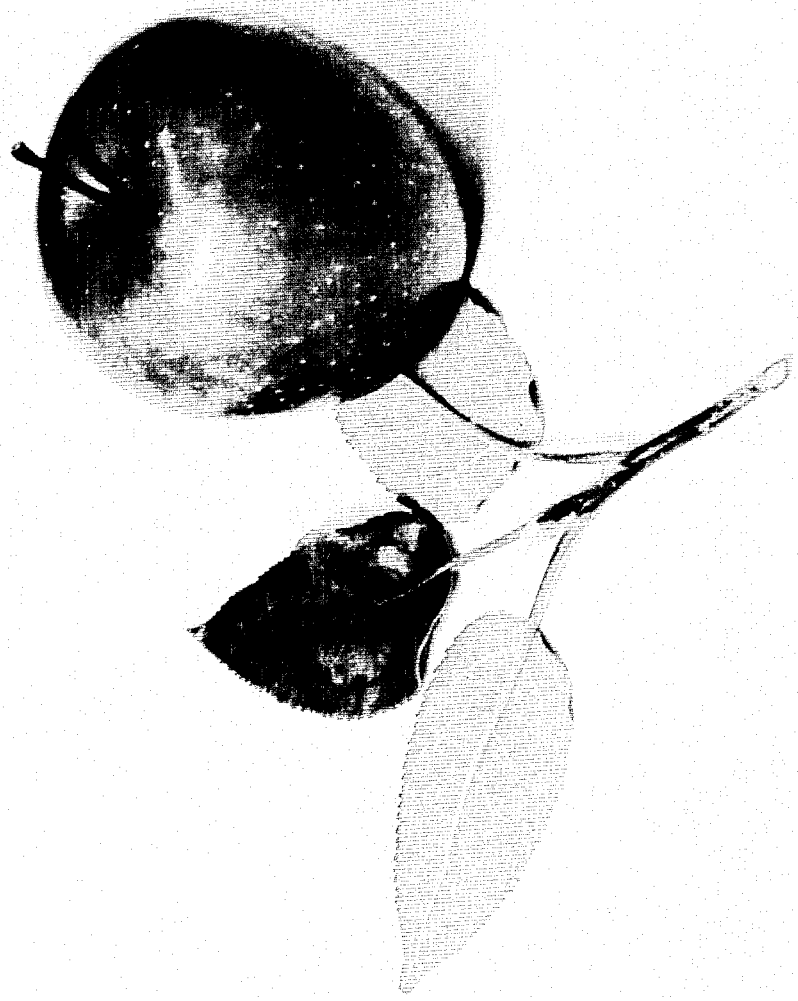

United States Patent Office

Plant Pat. 3,035
Patented Mar. 2, 1971

3,035

APPLE TREE

Corliss R. Maxam, 308 Beverly Road,
Barrington, Ill. 60010

Filed Mar. 29, 1968, Ser. No. 717,478
Int. Cl. A01h *5/03*
U.S. Cl. Plt.—35 1 Claim The present invention relates to a new and distinct variety of apple tree discovered amidst an orchard of Starking Delicious at Cobden, Ill. The fruit of the tree of the invention is of a deeper red color than the Starking Delicious and the color is uniform throughout. Furthermore, the stems are red in color. It was also noticed that all of the fruit matures at the same time. The obvious advantage of this, of course, is that all may be harvested at the same time.

The fruit of the present apple tree is of relatively large size and the size is relatively unaffected by sustained hot weather conditions. When the sepals divide, their color is typically Starking Delicious but when the petals begin to unfurl, they are slightly darker pink than the Starking Delicious.

This new variety has been asexually reproduced by grafting and it has been established that the distinct characteristics of the fruit prevail and are transmitted through succeeding propagations.

The new variety will now be described in detail with color terminology in accordance with color-eye wavelength measuring apparatus produced by Instrument Development Laboratories Division of Kollmorgen Corporation of Attleboro, Mass. In addition, other comparative color references are made. This detailed description is based upon observations made at Cobden, County of Union, Ill.

Dates of pickings: September 1, 1967

Tree: Standard size; great vigor (about 16–24 inches per year); productivity—heavy (27 bushels per year); regular bearer; ripening period—25 to 30 days after turning red; early reddening (first week of August); fragrance—aromatic.

Flowers: Prolific blossoms; large size. Color—white with tinge of pink; slightly darker than Starking Delicious.

Terminal growth: Dark Red.

Fruit: Maturity when described—hard ripe (date about September 1).

*Size.*—Uniform and large. Axial diameter—about 3½ inches. Transverse diameter—about 3 inches.

*Form.*—Right angle to axis—round conic. Along axis: ribbed.

*Cavity.*—Symmetrical. Depth—about ½ inch. Color—identical to rest of skin.

*Stem.*—Slender, about 1 inch to 1½ inches long of deep red color.

*Skin.*—Thick; smooth; tough (will not peel off when two sections are separated); waxy. Dots—evenly distributed and less prominent than Starking Delicious; skin color—to the naked eye appears to be evenly distributed and of a deep red color throughout; on the Kollmorgan scale, the fruit produced a relative intensity of 1274 at 400 nanometers, 1169 at 420 nanometers, 1007 at 440 nanometers, 1054 at 460 nanometers, 1188 at 480 nanometers, 1170 at 500 nanometers, 966 at 520 nanometers, 861 at 540 nanometers, 896 at 560 nanometers, 1210 at 580 nanometers, 1773 at 600 nanometers, 2270 at 620 nanometers, 2408 at 640 nanometers, 2560 at 660 nanometers, 2791 at 680 nanometers, and 3292 at 700 nanometers; on the color-eye scale, there was an X value of 1740, a Y value of 1277, and a Z value of 1080.

*Flesh.*—Juicy. Color—off-white (lighter than Starking Delicious). Texture—firm; not mealy (cellular structure smaller than Starking Delicious). Flavor—aromatic sweet, tastier than Starking Delicious. Aroma—distinct at a distance of 6 inches. Quality—prime.

*Core.*—Position: medium, core lines: meeting; axis: axile; carpels: surface tufted; cells: closed; shape: mucronate; bundle area: small size.

Seeds:

*Number.*—Average three plus one immature.

*Form.*—Asymmetrical, larger cross-sectional area, less tear-drop shaped, slightly shorter than Starking Delicious.

*Color.*—Darker than Starking Delicious.

*Sack.*—Seeds firmly held.

Leaves: Pinnate; petiole-red; main vein and secondary veins—red.

Use: Prime eating apple.

Keeping quality: Excellent.

Shipping quality: Excellent.

Disease and insect resistance: Typical to that of Starking Delicious.

I claim:

1. A new and distinct variety of apple tree, substantially as herein shown and described, characterized particularly as to novelty by fruit of uniform size and uniform deep red color with no markings, the fruit having a dark red stem, dark green leaves each having a light green underside, red petiole and red main and secondary veins, heavy productivity, uniform coloring habit of fruit throughout the tree with simultaneous maturation throughout the tree.

No references cited.

ROBERT E. BAGWILL, Primary Examiner